(12) United States Patent
Schudlo et al.

(10) Patent No.: US 11,145,060 B1
(45) Date of Patent: Oct. 12, 2021

(54) AUTOMATIC DETECTION OF VERTEBRAL DISLOCATIONS

(71) Applicant: International Business Machines Corporation, Armonk, NY (US)

(72) Inventors: Larissa Christina Schudlo, Boston, MA (US); Mark D. Bronkalla, Waukesha, WI (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/932,997

(22) Filed: Jul. 20, 2020

(51) Int. Cl.
*G06K 9/00* (2006.01)
*G06T 7/00* (2017.01)
(Continued)

(52) U.S. Cl.
CPC .............. *G06T 7/0016* (2013.01); *G06T 7/74* (2017.01); *G16H 30/20* (2018.01); *G06T 2207/10081* (2013.01); *G06T 2207/20081* (2013.01); *G06T 2207/20084* (2013.01); *G06T 2207/30012* (2013.01)

(58) Field of Classification Search
CPC ...................... G06T 7/0016; G06T 7/74; G06T 2207/10081; G06T 2207/20081; G06T 2207/20084; G06T 2207/30012; G16H 30/20
See application file for complete search history.

(56) References Cited

U.S. PATENT DOCUMENTS

| 5,944,664 A | 8/1999 | Hayashi |
| 2008/0216845 A1 | 9/2008 | De Bruijne |

(Continued)

FOREIGN PATENT DOCUMENTS

| CN | 103565449 A | 2/2014 |
| CN | 109730682 A | 5/2019 |

(Continued)

OTHER PUBLICATIONS

Lee et al., "Learning Radiologist's Step-by-Step Skill for Cervical Spinal Injury Examination: Line Drawing, Prevertebral Soft Tissue Thickness Measurement, and Swelling Detection", IEEE Access, vol. 6, pp. 55492-55500, 2018, 9 Pages.

(Continued)

*Primary Examiner* — Atiba O Fitzpatrick
(74) *Attorney, Agent, or Firm* — Donald G. Weiss

(57) ABSTRACT

In an approach to automatic detection of vertebral dislocations, training data is received, where the training data includes an ordered sequence of radiographic image patches of vertebrae and intervertebral spaces, and location data for each vertebra and each intervertebral space. Location deep learning models are trained to detect a location of each vertebra and each intervertebral space from the training data. Classification deep learning models are trained to classify an ordered sequence of image patches to identify vertebral anomalies of the vertebrae and the intervertebral spaces from the training data. Responsive to receiving radiographic image files, the location deep learning models and the classification deep learning models are applied to the radiographic image files to create a condition assessment.

20 Claims, 8 Drawing Sheets

(51) Int. Cl.
*G06T 7/73* (2017.01)
*G16H 30/20* (2018.01)

(56) References Cited

U.S. PATENT DOCUMENTS

| | | | |
|---|---|---|---|
| 2016/0113612 A1 | 4/2016 | Sedlmair | |
| 2019/0021677 A1* | 1/2019 | Grbic | A61B 5/7292 |
| 2019/0088360 A1 | 3/2019 | Goble | |
| 2021/0133962 A1* | 5/2021 | Xin | A61B 5/4566 |

FOREIGN PATENT DOCUMENTS

| | | | |
|---|---|---|---|
| DE | 102006041619 A1 | 4/2007 | |
| RU | 2145188 C1 | 2/2000 | |
| RU | 2263470 C1 | 11/2005 | |
| RU | 2358651 C1 | 6/2009 | |

OTHER PUBLICATIONS

Lai et al., "Spatial Regularized Classification Network for Spinal Dislocation Diagnosis", Machine Learning in Medical Imaging, MLMI 2019, Lecture Notes in Computer Science, vol. 11861, Springer, Cham, pp. 9-17, 2019, 4 Pages.

Bar et al., "Compression Fractures Detection on CT", The Blavatnik School of Computer Science, Tel Aviv University, Zebra Medical Vision, arXiv:1706.01671v1, [cs.CV], Jun. 6, 2017, 8 Pages.

Burns et al., "Vertebral Body Compression Fractures and Bone Density: Automated Detection and Classification on CT Images", RSNA Radiology, vol. 284, No. 3, Mar. 16, 2017, 21 Pages.

Guglielmi et al., "Assessment of osteoporotic vertebral fractures using specialized workflow software for 6-point morphometry", European Journal of Radiology, vol. 70, Issue 1, Apr. 2009, 2 Pages.

Duryea et al., "Neural network based algorithm to quantify joint space width in joints of the hand for arthritis assessment", Medical Physics, 27(5), pp. 1185-1194, 2000, 11 Pages.

Jamaludin, et al., "Automation of reading of radiological features from magnetic resonance images (MRIs) of the lumbar spine without human intervention is comparable with an expert radiologist", Issls Prize in Bioengineering Science 2017, Eur Spine J. 2017;26(5),1374-1383. doi:10.1007/s00586-017-4956-3, Feb. 6, 2017, 2 Pages.

Mahendran, et al., "Automatic Fracture Detection Using Classifiers-A Review", IJCSI International Journal of Computer Science Issues, vol. 8, Issue 6, No. 1, ISSN (Online): 1694-0814, Nov. 2011, 6 Pages.

Nicolaes et al., "Detection of vertebral fractures in CT using 3D Convolutional Neural Networks", arXiv:1911.01816v1, [eess.IV], Nov. 5, 2019, 13 pages.

Stanley et al., "Image Analysis Techniques for the Automated Evaluation of Subaxial Subluxation in Cervical Spine X-Ray Images", Proc. 17th IEEE Symposium on Computer-Based Medical Systems (2004, Bethesda, MD), vol. 17, pp. 204-209, Jun 2004, 7 Pages.

Raghavendra et al., "Automated system for the detection of thoracolumbar fractures using a CNN architecture", Article, Future Generation Computer Systems—The International Journal of Escience, vol. 85, pp. 184-189, DOI: 10.1016/j.future.2018.03.023, Aug. 2018, 2 Pages.

Arif, Al, "Fully automatic image analysis framework for cervical vertebra in X-ray images", Doctoral thesis, Department of Computer Science, University of London, Jan. 2018, 260 Pages.

Koompairojn et al., "Automatic Classification System for Lumbar Spine X-ray Images", 19th IEEE Symposium on Computer-Based Medical Systems (CBMS'06), Salt Lake City, UT, 2006, pp. 213-218, 6 Pages.

\* cited by examiner

US 11,145,060 B1

AUTOMATIC DETECTION OF VERTEBRAL DISLOCATIONS

BACKGROUND

The present invention relates generally to the field of radiation diagnosis, and more particularly to automatic detection of vertebral dislocations.

The spine is made of 33 individual bones stacked one on top of the other. The spine provides the main support for the human body, allowing a person to stand upright, bend, and twist, while protecting the spinal cord from injury. The spine consists of 24 moveable vertebrae in three main sections—cervical (neck, numbered C1-C7), thoracic (mid back, numbered T1-T12), and lumbar (lower back, numbered L1-L5). The spine also contains the sacrum, which contains five fused bones, and the coccyx, which contains four fused bones.

An X-ray is a diagnostic test that uses radiation to produce images of the bones and organs of the body. Spine X-rays provide detailed images of the bones of the spine. During an X-ray, a focused beam of radiation is passed through the body, and a black-and-white image is recorded on special film or, in the case of modern digital X-rays, a digital detector which is fed into a computer. X-rays work because body tissues vary in density, and therefore each tissue allows a different amount of radiation to pass through. Bones, for example, are very dense, and most of the radiation is prevented from passing through to the film or detector. As a result, bones appear white on an X-ray image. Tissues that are less dense—such as the lungs—allow more of the X-rays to pass through to the film or detector and appear on the image in shades of gray.

Spine X-rays are typically taken in either the anteroposterior (front to back) or the posteroanterior (back to front) view, commonly referred to as an AP/PA view, or the lateral (side) view.

Computed tomography (CT or CT scan) is a noninvasive diagnostic imaging procedure that uses a combination of X-rays and computer technology to produce axial images, often called slices, of the body. In a CT scan, the X-ray beam moves in a circle around the body. The X-ray information is sent to a computer that interprets the X-ray data and displays it in a two-dimensional (2D) form on a monitor. Digital geometric processing is used to further generate a three-dimensional (3D) volume of the inside of the subject from the series of 2D images taken around a single axis of rotation during the CT scan.

CT scans are more detailed than standard X-rays. CT produces data that can be manipulated in order to demonstrate various bodily structures based on their ability to absorb the X-ray beam. CT scans of the spine can provide more detailed information about the vertebrae than standard X-rays, thus providing more information related to injuries and/or diseases of the spine.

SUMMARY

Embodiments of the present invention disclose a method, a computer program product, and a system for automatic detection of vertebral dislocations. In one embodiment, training data is received, where the training data includes an ordered sequence of radiographic image patches of vertebrae and intervertebral spaces, and location data for each vertebra and each intervertebral space. Location deep learning models are trained to detect a location of each vertebra and each intervertebral space from the training data. Classification deep learning models are trained to classify an ordered sequence of image patches to identify vertebral anomalies of the vertebrae and the intervertebral spaces from the training data. Responsive to receiving radiographic image files, the location deep learning models and the classification deep learning models are applied to the radiographic image files to create a condition assessment.

DETAILED DESCRIPTION

Figure 1:
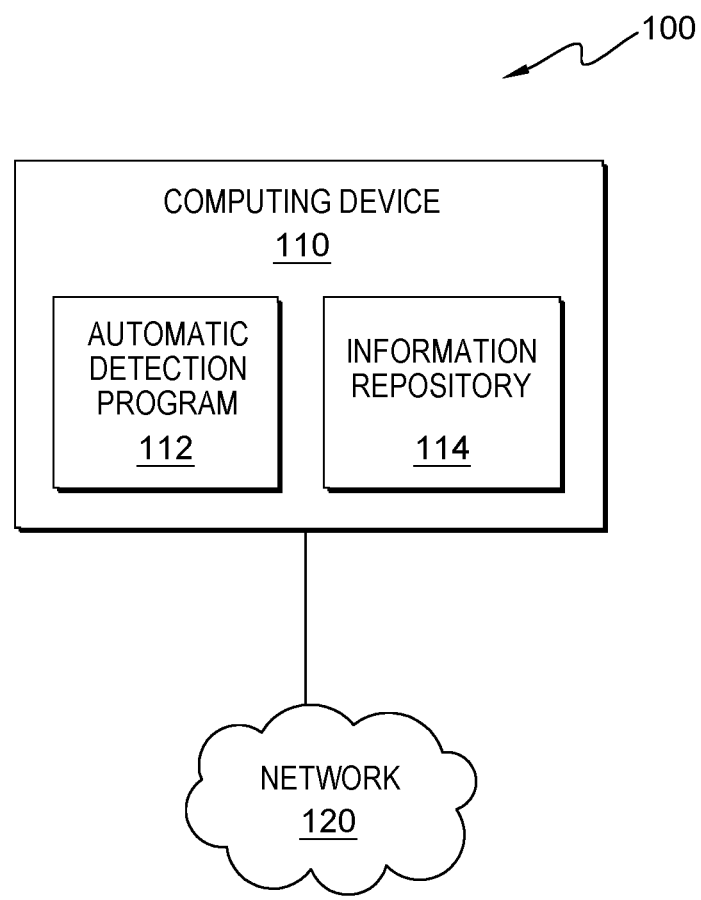
FIG. 1 is a functional block diagram illustrating a distributed data processing environment, in accordance with an embodiment of the present invention.

Radiographic investigation is critical for identifying, diagnosing, and managing spinal abnormalities. These abnormalities may be due to chronic or degenerative conditions or acute trauma. Plain x-ray films, which are projection x-ray images, are a quick way to assess the spine, and are readily available in most hospitals, trauma centers and even remote locations. This type of imaging is useful to perform initial screening of spinal abnormalities and to indicate the need for additional imaging. These images are also part of the triage of acute cases where the patient may be in danger of permanent disability or death due to dislocations severing the spinal cord or major arteries, particularly in the neck. These types of images, however, often underestimate the degree of injury, thus challenging the ability of a radiologist to detect abnormalities. In addition, when used in trauma treatment the first reader of the study is typically not a radiologist, but an emergency provider. Consequently, fractures and lesions are often missed, or the error may only be caught after a patient has already been discharged. Due to these factors, Computed Tomography (CT) has become the recommended modality of choice for diagnosis of spinal fractures. However, in many cases there is still a plain film radiograph taken initially even when CT is available. The availability, speed of acquisition, and coverage of a large portion of anatomy (e.g., a chest radiograph) favor the plain film radiograph when assessing potentially multiple injuries in a trauma case. In some locales (e.g., a battlefield or a developing country), CT imaging may not be available or may require transportation to a remote facility, whereas plain film x-rays are generally available. Even when CT is available, a local reading radiologist may not be available thereby leading to delays in treatment or initial interpretations being performed by non-radiologists.

Two main types of injuries to vertebrae are fractures and dislocations. A fracture is typically seen as a change in morphological shape or loss in height of a vertebrae, while a dislocation is a misalignment in the sequence of vertebrae. Another type of injury to the spine is a subluxation, where the joints in the back part of the vertebrae are weakened due to injured spinal muscle or ligaments, yielding a partial dislocation or misalignment of the vertebrae. There are multiple types of fractures including common examples such as compression fractures, burst flexion-distraction fractures, and fracture-dislocations. In some cases, there are torn ligaments that are present and can sometimes be visualized even if there is no vertebral fracture, dislocation, or subluxation. The presence of the torn or detached ligaments is indicative of instability of the spine which may be acute.

The cervical spine is the most mobile portion of the spine and therefore most susceptible to injury, accounting for the majority of dislocations. This is also exacerbated by the mass of the head. A dislocation can be initially detected on chest x-rays (either frontal or lateral). Plain x-rays of the spine, including the cervical spine, are essential to evaluate a spinal fracture or dislocation. Non-displaced or minimally displaced factures or instability are challenging to discern on plain x-rays. Once suspected, this type of injury is then typically confirmed via CT and MRI.

Detecting spinal dislocations or subluxations requires consideration of the relative vertebral alignment along the spine, as well as changes in intervertebral spacing. Typically, the spacing both in terms of absolute distance and angular alignment between adjacent vertebrae is not constant. Notably the angular variation varies widely between individuals. Consider the issue of curvature of the spine, whether scoliosis, which is a sideways curvature, kyphosis, which is a forward curvature, or lordosis, which is lack of curvature or too straight of a spine. These curvatures are further illustrated in FIGS. 3a-3c below. There is a wide variation in the degree of curvature and the curvature should not be falsely flagged as a subluxation or dislocation. Using a simple classifier that is trained on a range of "normal" spines would have too broad a range of "normal" to be useful.

The present invention is a method, computer program product, and system for automatic detection of vertebral dislocations in both plain film radiograph images, as well as 3D images from CT scans, using a combination of image processing and artificial intelligence techniques. In order to better discern the misalignment as being abnormal, the present invention analyzes the relationship of the local vertebral spacing in the context of the shape of the spine of that particular patient. The present invention is trained to cover a variety of anatomical variations that are not indicative of a fracture, dislocation, or subluxation, as well as a set with these defects annotated. This increases the ability to discern between the "normal"/non-subluxed/non-fractured variations and those images with these defects present. This is done both within the context of the current study as well as part of a serial comparison versus previous image files from prior studies of the same region(s) of the same patient.

In an embodiment, to detect a dislocation or subluxation, the present invention evaluates the relative shift of vertebrae in the spinal column to determine abnormal changes or positioning. To perform a fully automated detection of vertebral dislocations and subluxations, the present invention first localizes the vertebral centers and intervertebral disc spaces. Image patches corresponding to the intervertebral disc space as well as the vertebrae above and below the intervertebral disc space are extracted to capture the relative alignment of adjacent vertebrae. Either the full vertebrae above and below the intervertebral disc space or a portion of the full vertebrae above and below the intervertebral disc space (e.g., the bottom half of a vertebra, the disc space, and the top half of the next vertebra) are extracted. Next, the ordered sequence of the volume of sequential images are passed to a classifier that analyzes the images to identify changes in intervertebral spacing and vertebral alignment along the spine. In an embodiment, the classifier is a Recurrent Neural Network (RNN). In an embodiment, the classifier RNN is a Long Short-Term Memory (LSTM). In other embodiments, other classification methods are used as discussed below. This procedure in described in detail in FIG. 6 below.

In an embodiment, there are multiple views available (e.g., AP/PA and lateral), and the present invention performs the above analysis on each of the images and then compares the results, reporting the most severe findings. In another embodiment, all the findings of the analysis are reported.

In an embodiment, the present invention assigns metrics to the vertebral spacing, angular displacement, and offset between the vertebral pairs to denote the degree of change and performs a comparison between the current and one or more prior studies.

In an embodiment, the present invention provides an output to the clinician, which is graphically represented, for example, a heat map or graphical overlay style. In another embodiment, the out to the clinician includes the labeled location of the subluxation or dislocation (e.g., L1-L2).

In an embodiment, the present invention provides an alert or notification to standard medical information systems, for example the Electronic Medical Records system (EMR) or the Picture Archiving And Communication System (PACS), when a dislocation or subluxation is detected.

In an embodiment, the processing includes the option for triples of vertebrae, in addition to pairs.

In another embodiment, the input to the present invention is a 3D image, such as a CT scan. In clinical practice, frontal and lateral chest or spinal X-rays are ordered for a variety of reasons, and are frequently followed by CT scans. As explained above for plain film radiograph images, in these routinely performed CT scans dislocations and subluxations are frequently missed by clinicians. In an embodiment, the pipeline mimics the diagnostic process of clinicians to identify vertebral dislocation and subluxations by isolating each individual vertebra and adjacent intervertebral disc spaces, evaluating visibility, and considering sufficiently visible successive vertebrae with the intervertebral or disc space as an ordered sequence in a time-distributed inference model to analyze their relative morphologies and positioning/alignment to identify dislocations. In the present invention, the pipeline does not rely on complete vertebrae or disc space visibility or depend on a specific number of visible vertebrae, but instead accommodates variability in both these factors. Additionally, as in the above for plain film radiograph images, the present invention is designed to work despite widely varying degrees of spinal curvature, adapting to the shape of the particular patient.

In this embodiment, to perform a fully automated detection of vertebral dislocations and subluxations, the present invention first localizes the vertebral body centers and intervertebral disc space. In another embodiment, each of the vertebrae visible in the field of view (FOV) of the CT scan is labelled (C1-L5). Quantitative parameters such as intervertebral disc sizes and volumes, and Hounsfield unit (HU) value in the center of vertebral bodies are extracted. The Hounsfield unit is a relative quantitative measurement of radio density used by radiologists in the interpretation of CT images. They are used during CT reconstruction to produce a grayscale image. HU values in the centers of vertebral bodies are indicative of low bone density. These values are used as features in the machine learning (ML) methods used for automatic detection of dislocations, as discussed in more detail in FIG. 7 below. CT subvolumes (3D image patches) containing vertebrae are identified. Each subvolume will contain a vertebra that is to be classified as well as at least two other adjacent vertebrae to capture the relative alignment of adjacent vertebrae. For example, when determining dislocation involving T11, the subvolume would contain T10-T11-T12 or T9-T10-T11-T12-L1, and so on. For the case of three vertebrae subvolume, e.g., T10-T11-T12, the subvolume could include the full vertebrae above (T10) and below (T12) of the vertebrae in question (T11) or just a portion of the vertebrae above and below the vertebrae in question (e.g., the bottom half of T10, the disc space, T11, the disc space, and the top half of T12). The subvolumes are aligned either along image axes or in a local direction defined by the orientation of the vertebrae in question. Subvolumes are either cuboids or cylinders. Next, 2d projections are created from the CT sub-volumes (similar to volumetric to planar data augmentation used for the 2D images above). The number of generated 2D projections for each sub-volume and angles defining of those projections is in a range from 1 to 64. The projections are created using mean, maximum intensity projections (MIP), and sum weighted by an HU-number derived opacity function. This procedure in described in detail in FIG. 7 below.

In a first embodiment, classification and machine learning include using quantitative values, 3D image patches, and 2D projections of sequential data in a classifier that considers the ordered sequence to identify changes in intervertebral spacing and vertebral alignment along the spine. In some embodiments, this is performed with an RNN classifier such as LSTM, 3D Convolutional Neural Network (CNN)+ LSTM, or time-distributed CNN+LSTM that can be applied to a sequence of images (whole spine approach).

In another embodiment, classification and machine learning include using quantitative values, 3D image patches, and 2D projections of sequential data to detect dislocation on a per spine section (cervical, thoracic, and lumbar) basis, which uses different classifiers for different sections. Any other different sectioning of the spine can also be used. In yet another embodiment, separate classifiers are used for each different vertebra, and sequence machine learning is not used.

In an embodiment, data is used to create a binary classifier (dislocation present or not) and data from all vertebrae is used to train a single classifier.

In an embodiment, where sagittal and coronal thick slab images (or other orientations) are created, the inference model is retrained specifically for these images rather than the plain film x-rays.

FIG. 1 is a functional block diagram illustrating a distributed data processing environment, generally designated 100, suitable for operation of automatic detection program 112 in accordance with at least one embodiment of the present invention. The term "distributed" as used herein describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes computing device 110 connected to network 120. Network 120 can be, for example, a telecommunications network, a local area network (LAN), a wide area network (WAN), such as the Internet, or a combination of the three, and can include wired, wireless, or fiber optic connections. Network 120 can include one or more wired and/or wireless networks that are capable of receiving and transmitting data, voice, and/or video signals, including multimedia signals that include voice, data, and video information. In general, network 120 can be any combination of connections and protocols that will support communications between computing device 110 and other computing devices (not shown) within distributed data processing environment 100.

Computing device 110 can be a standalone computing device, a management server, a web server, a mobile computing device, or any other electronic device or computing system capable of receiving, sending, and processing data. In an embodiment, computing device 110 can be a laptop computer, a tablet computer, a netbook computer, a personal computer (PC), a desktop computer, a personal digital assistant (PDA), a smart phone, or any programmable electronic device capable of communicating with other computing devices (not shown) within distributed data processing environment 100 via network 120. In another embodiment, computing device 110 can represent a server computing system utilizing multiple computers as a server system, such as in a cloud computing environment. In yet another embodiment, computing device 110 represents a computing system utilizing clustered computers and components (e.g., database server computers, application server computers) that act as a single pool of seamless resources when accessed within distributed data processing environment 100.

In an embodiment, computing device 110 includes automatic detection program 112. In an embodiment, automatic detection program 112 is a program, application, or subprogram of a larger program for automatic detection of vertebral dislocations. In an alternative embodiment, automatic detection program 112 may be located on any other device accessible by computing device 110 via network 120.

In an embodiment, computing device 110 includes information repository 114. In an embodiment, information repository 114 may be managed by automatic detection program 112. In an alternate embodiment, information repository 114 may be managed by the operating system of the device, alone, or together with, automatic detection program 112. Information repository 114 is a data repository that can store, gather, compare, and/or combine information. In some embodiments, information repository 114 is located externally to computing device 110 and accessed through a communication network, such as network 120. In some embodiments, information repository 114 is stored on computing device 110. In some embodiments, information repository 114 may reside on another computing device (not shown), provided that information repository 114 is accessible by computing device 110. Information repository 114 includes, but is not limited to, X-ray image data, CT scan image data, EMR data, PACS data, user data, system configuration data, and other data that is received by automatic detection program 112 from one or more sources, and data that is created by automatic detection program 112.

Information repository 114 may be implemented using any volatile or non-volatile storage media for storing information, as known in the art. For example, information repository 114 may be implemented with a tape library, optical library, one or more independent hard disk drives, multiple hard disk drives in a redundant array of independent disks (RAID), solid-state drives (SSD), or random-access memory (RAM). Similarly, the information repository 114 may be implemented with any suitable storage architecture known in the art, such as a relational database, an object-oriented database, or one or more tables.

Figure 2A:
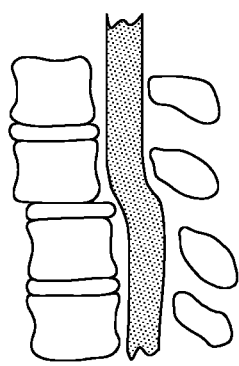
FIG. 2a is an illustration of a vertebral subluxation, in accordance with an embodiment of the present invention.
Figure 2B:
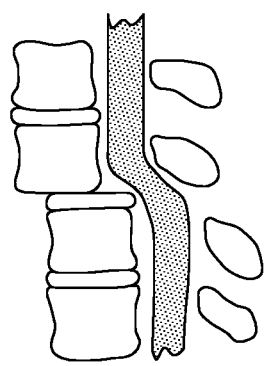
FIG. 2b is an illustration of a vertebral dislocation, in accordance with an embodiment of the present invention.
Figure 2C:
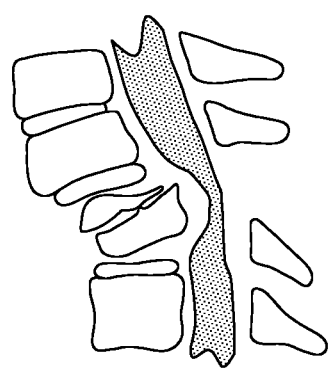
FIG. 2c is an illustration of a vertebral fracture-dislocation, in accordance with an embodiment of the present invention.

FIGS. 2a, 2b, and 2c are examples of the types of abnormalities detected by automatic detection program 112. FIG. 2a is an illustration of a subluxation, where the joints in the back part of the vertebrae are weakened due to injured spinal muscle or ligaments, yielding a partial dislocation or misalignment of the vertebrae. FIG. 2b is an illustration of a dislocation, where two or more adjoining vertebrae become abnormality separated from each other and the vertebra may 'lock' over each other on one or both sides. FIG. 2c is an illustration of a fracture-dislocation, which occurs when there is a fracture and a dislocation of the vertebrae.

Figure 3C:
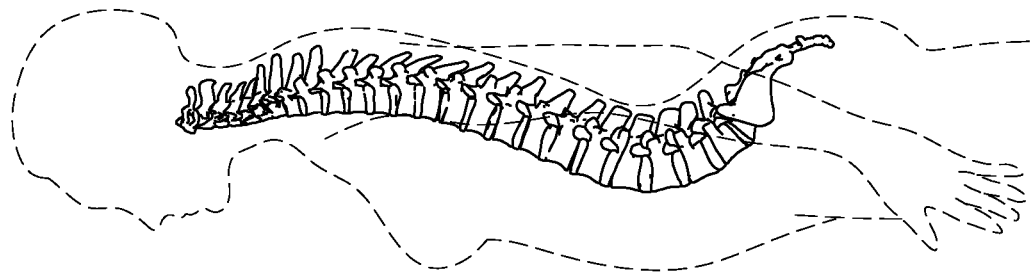
FIG. 3c is an illustration of lordosis, which is lack of curvature of the spine, in accordance with an embodiment of the present invention.
Figure 3B:
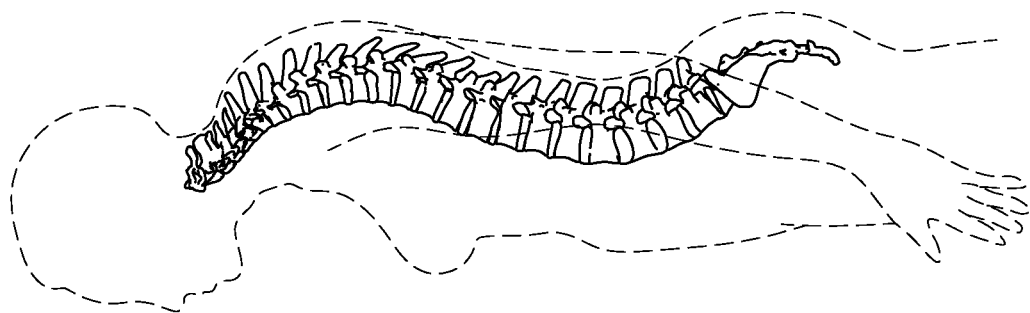
FIG. 3b is an illustration of kyphosis, which is a forward curvature of the spine, in accordance with an embodiment of the present invention.
Figure 3A:
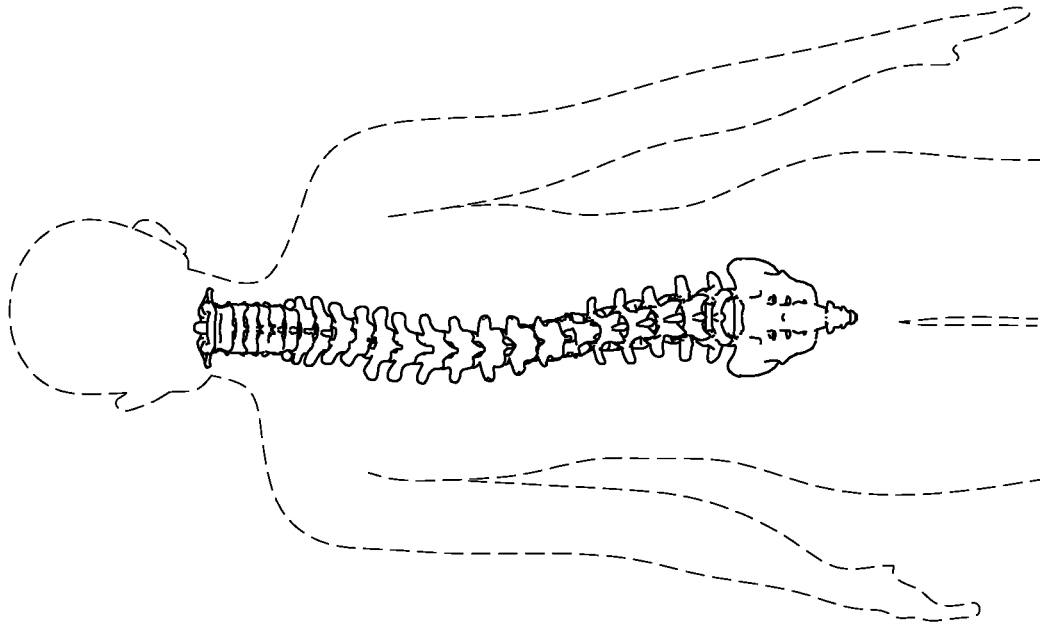
FIG. 3a is an illustration of scoliosis, which is a sideways curvature of the spine, in accordance with an embodiment of the present invention.

FIGS. 3a, 3b, and 3c are illustrations of the wide variation in the degree of curvature that can be found in the spine. These forms of curvature should not be falsely flagged as a subluxation or dislocation. FIG. 3a is an illustration of scoliosis, which is a sideways curvature of the spine. FIG. 3b is an illustration of kyphosis which is a forward curvature of the spine. FIG. 3c is an illustration of lordosis, which is lack of curvature of the spine, in other words, the spine is too straight.

Figure 4:
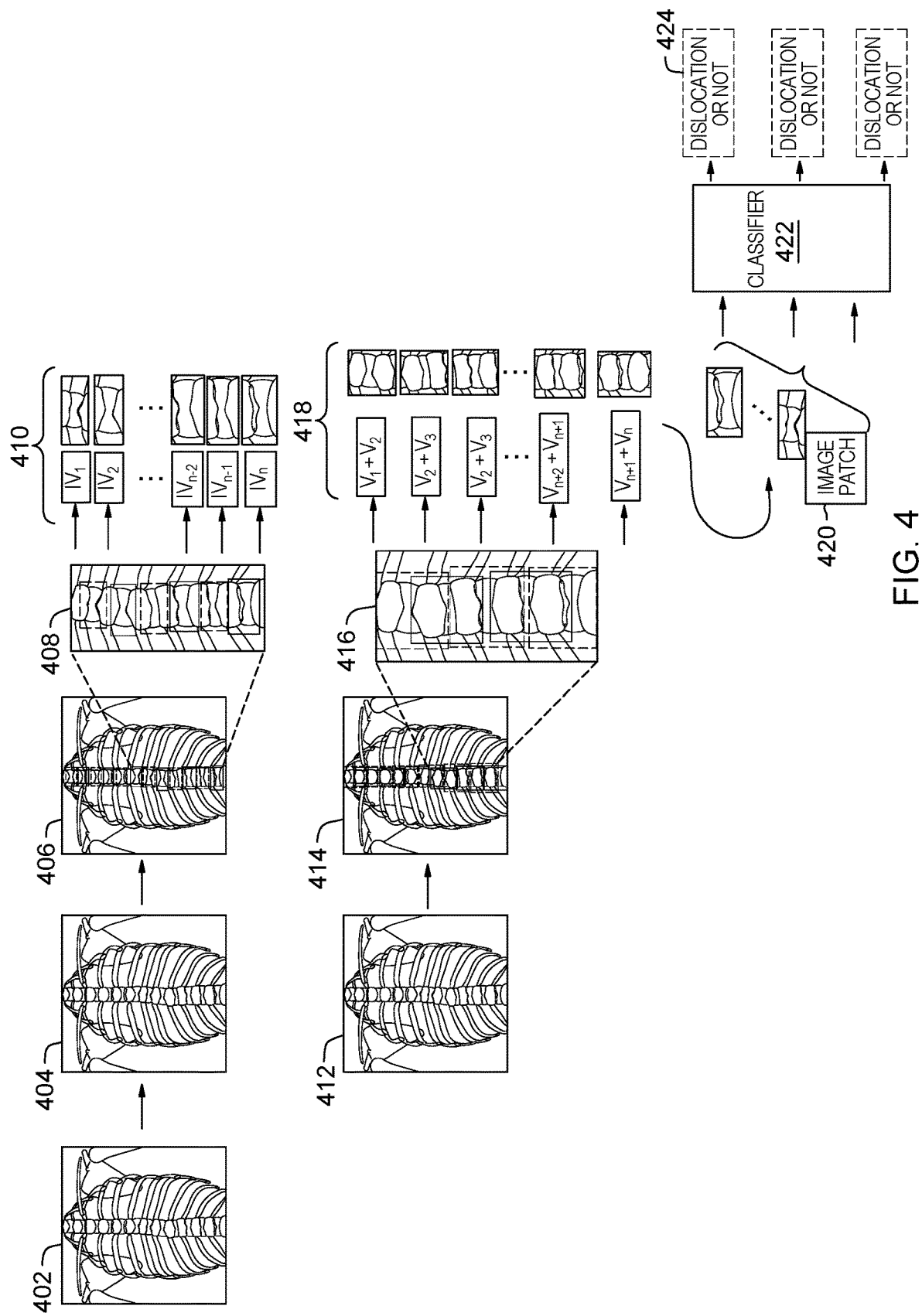
FIG. 4 is a description of the algorithm to detect a dislocation or subluxation, in accordance with an embodiment of the present invention.

FIG. 4 is a visual illustration of the steps in one embodiment of the algorithm to detect a dislocation or subluxation by automatic detection program 112. In step 402, automatic detection program 112 receives the image. In step 404, automatic detection program 112 detects the location of each vertebrae. In step 406, automatic detection program 112 extracts the image patches for intervertebral spaces. Each intervertebral space is individually extracted by automatic detection program 112 as the space between each vertebrae detected in step 404. Intervertebral space image patches 408 depicts a closeup of the isolation of individual intervertebral space in step 406. Item 410 depicts the individual image patches that were extracted in step 406. In step 412, automatic detection program 112 detects the intervertebral spaces. The location of each intervertebral space in the received image is detected by automatic detection program 112. In step 414, automatic detection program 112 extracts the image patch for each individual vertebra. Each individual vertebra is extracted by automatic detection program 112 as occupying the area between each pair of adjacent intervertebral spaces detected in step 412. Item 416 depicts a closeup of the isolation of individual vertebra in step 414. Vertebral image patches 418 depicts the individual image patches that were extracted in step 414. Image patches 420 represents the images patches extracted from the image received in step 402, which are then passed to classifier 422. The various forms of classification used by automatic detection program 112 are discussed in FIGS. 5 and 6 below. Item 424 represents the decisions for image patches 420 at the output of the classifier.

Figure 5:
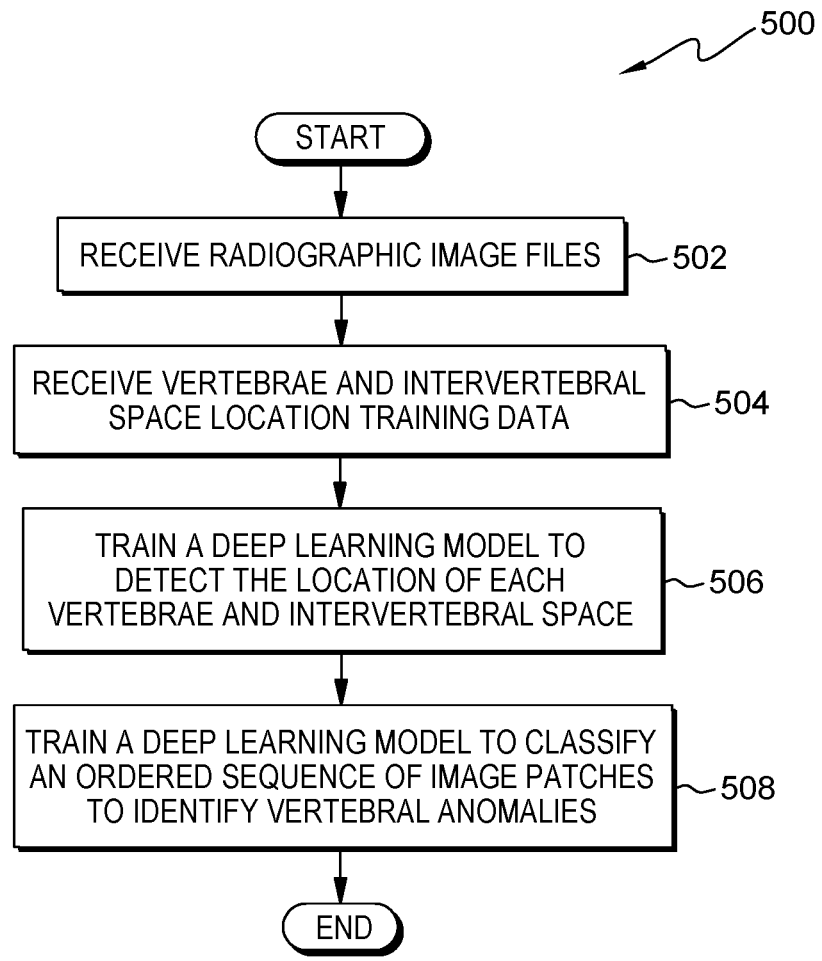
FIG. 5 is a flowchart diagram depicting operational steps for the automatic detection program for training the machine learning algorithms, on the distributed data processing environment of FIG. 1, in accordance with an embodiment of the present invention.

FIG. 5 is a flow chart diagram of workflow 500 depicting operational steps for automatic detection program 112 for training the machine learning algorithms. In an alternative embodiment, the steps of workflow 500 may be performed by any other program while working with automatic detection program 112. In an embodiment, automatic detection program 112 receives radiographic image files to use to train the deep learning models. In an embodiment, automatic detection program 112 receives training data consisting of location data for each vertebrae and each intervertebral space in the radiographic images to train the deep learning models. In an embodiment, automatic detection program 112 uses the radiographic images and the training data to train a deep learning model to detect the location of each vertebra and each intervertebral space in the training images. In an embodiment, automatic detection program 112 uses the radiographic images and the training data to train a deep learning model that considers the ordered sequence of image patches to utilize sequential and morphological characteristics within an input images to identify vertebral dislocations and subluxations.

It should be appreciated that embodiments of the present invention provide at least for training the machine learning models for the automatic detection of vertebral dislocations. However, FIG. 5 provides only an illustration of one implementation and does not imply any limitations with regard to the environments in which different embodiments may be implemented. Many modifications to the depicted environment may be made by those skilled in the art without departing from the scope of the invention as recited by the claims.

It should be appreciated that the process depicted in FIG. 5 illustrates one possible iteration of the section of code performed by automatic detection program 112 for training the machine learning models, which repeats each time each time additional training data is received by automatic detection program 112.

Automatic detection program 112 receives radiographic image files (step 502). In an embodiment, automatic detection program 112 receives radiographic image files to use to train the deep learning models. In an embodiment, the radiographic image files are plain film radiograph images. In another embodiment, the radiographic image files are 3D images from CT scans. In yet another embodiment, the radiographic image files are any combination of 2D and 3D image files that are appropriate for teaching the deep learning models as would be known to a person of skill in the art.

Automatic detection program 112 receives vertebrae and intervertebral space location training data (step 504). In an embodiment, automatic detection program 112 receives training data to train the deep learning models. The training data consists of location data for each vertebrae and each intervertebral space in the radiographic images received in step 502.

Automatic detection program 112 trains a deep learning model to detect the location of each vertebra and intervertebral space (step 506). In an embodiment, automatic detection program 112 uses the radiographic images received in step 502 and the training data received in step 504 to train a deep learning model to detect the location of each vertebra and each intervertebral space in the training images. In an embodiment, automatic detection program 112 creates deep learning models to detect the location of each vertebra and intervertebral space for each different view that is to be analyzed, e.g., frontal view and lateral view.

Automatic detection program 112 trains a deep learning model to classify an ordered sequence of image patches to identify vertebral anomalies (step 508). In an embodiment, automatic detection program 112 uses the radiographic images received in step 502 and the training data received in step 504 to train a deep learning model that considers the ordered sequence of image patches extracted in step 504 to utilize sequential and morphological characteristics within an input images to identify vertebral dislocations and subluxations. In an embodiment, automatic detection program 112 trains deep learning models to classify an ordered sequence of image patches to identify vertebral anomalies for each different view that is to be analyzed, e.g., frontal view and lateral view.

In an embodiment, automatic detection program 112 trains the deep learning model to identify one or more existing conditions, where the one or more existing conditions include foreign objects, spinal hardware, external fixation devices, and spinal correction material. In an embodiment, automatic detection program 112 excludes these existing conditions when analyzing the received radiograph image file for analysis.

In an embodiment, automatic detection program 112 ends for this cycle.

Figure 6:
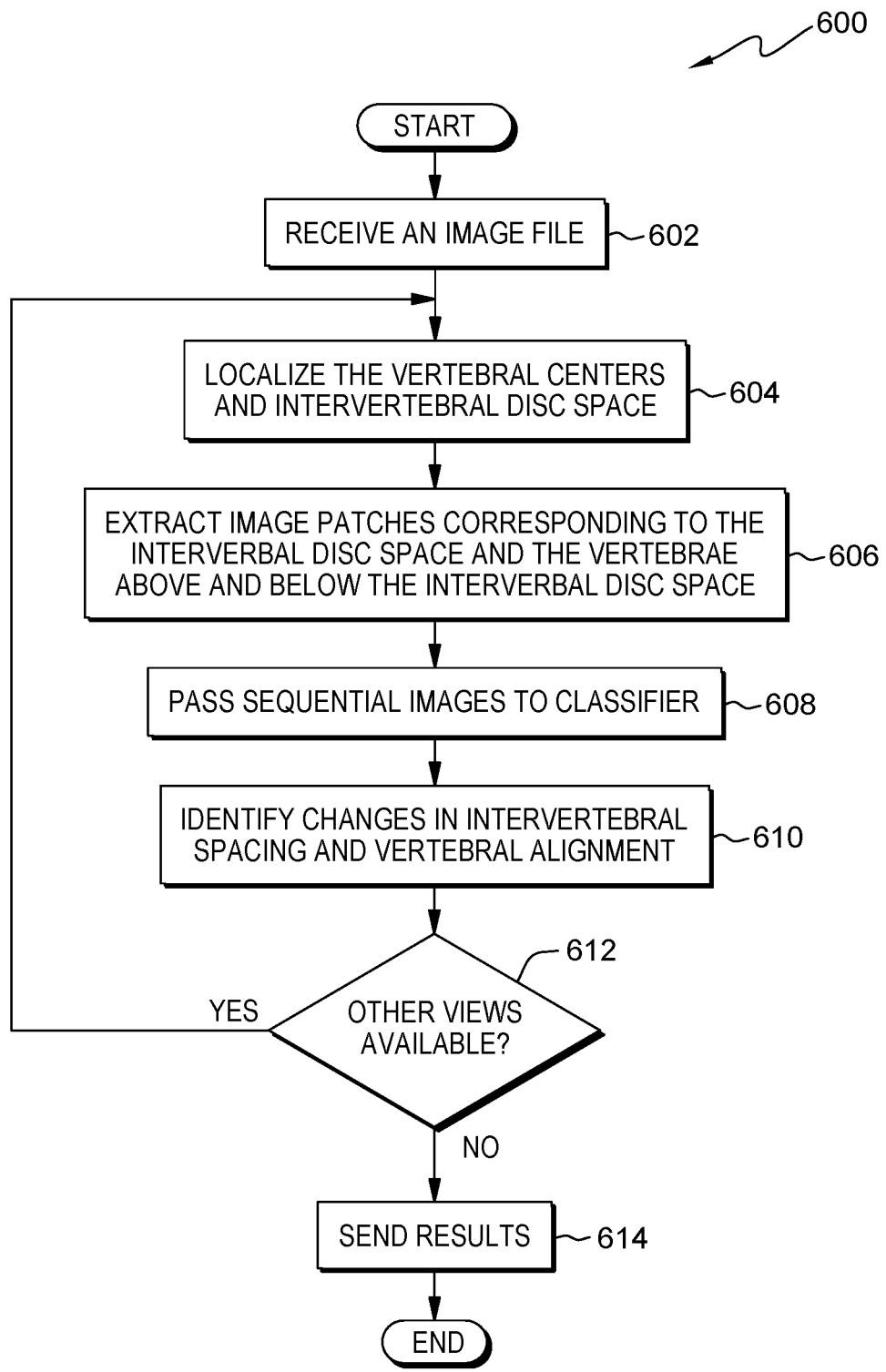
FIG. 6 is a flowchart diagram depicting operational steps for the automatic detection program for automatic detection of vertebral dislocations in 2D images, on the distributed data processing environment of FIG. 1, in accordance with an embodiment of the present invention.

FIG. 6 is a flow chart diagram of workflow 600 depicting operational steps for automatic detection program 112 for automatic detection of vertebral dislocations in 2D images. In an alternative embodiment, the steps of workflow 600 may be performed by any other program while working with automatic detection program 112. In an embodiment, automatic detection program 112 receives an image file for analysis. In an embodiment, automatic detection program 112 detects the vertebrae and the intervertebral spaces and localizes the boundaries of each vertebrae. In an embodiment, automatic detection program 112 extracts image patches corresponding to the intervertebral disc space as well as the vertebrae above and below the intervertebral disc space to capture the relative alignment of adjacent vertebrae. In an embodiment, automatic detection program 112 passes the image patches to a classifier, for example, classifier 422 from FIG. 4, to analyze the images. In an embodiment, automatic detection program 112 detects abnormalities in the intervertebral spacing and vertebral alignment. In an embodiment, automatic detection program 112 determines if there are any additional views to analyze. In an embodiment, automatic detection program 112 sends the results.

It should be appreciated that embodiments of the present invention provide at least for automatic detection of vertebral dislocations. However, FIG. 6 provides only an illustration of one implementation and does not imply any limitations with regard to the environments in which different embodiments may be implemented. Many modifications to the depicted environment may be made by those skilled in the art without departing from the scope of the invention as recited by the claims.

It should be appreciated that the process depicted in FIG. 6 illustrates one possible iteration of the section of code performed by automatic detection program 112 for automatic detection of vertebral dislocations in 2D images, which repeats each time each time a new 2D image file is received by automatic detection program 112.

Automatic detection program 112 receives an image file (step 602). In an embodiment, automatic detection program 112 receives an image file for analysis. The format of the image file can be, for example, DICOM, NIfTI, Minc, or Analyze. In other embodiments, any appropriate image file format may be used.

Automatic detection program 112 localizes the vertebral centers and intervertebral disc space (step 604). In an embodiment, automatic detection program 112 detects the vertebrae and the intervertebral spaces and localizes the boundaries of each vertebra. Various techniques are used to prepare and enhance the raw image for analysis, including image quality assessment, view detection, image normalization, down sampling, image filtering, windowing, and edge detection.

In an embodiment, a segmentation model (e.g., UNet) is used segment/detect each rib in the image, particularly in the regions connecting each rib and spine. In an embodiment, a segmentation model (e.g., UNet) is also used to segment the spine in the image.

In an embodiment, automatic detection program 112 uses an object detection model to detect the location of each vertebra and the adjacent intervertebral disc space and to extract image patches. These image patches are centered on, and include, each fully visible intervertebral disc space and the adjacent vertebrae in the image. This model uses information from the rib and spine segmentation to ensure the location of each intervertebral disc space is anatomically feasible (i.e. within the spine, and between pairs of ribs). Each patch includes a pair of vertebrae, as well as the intervertebral disc space between the pair of vertebrae. The object detection model may be, for example, Mask R-CNN (Region-based CNN), or a segmentation model such as UNet.

In an embodiment, automatic detection program 112 uses the deep learning model trained in step 506 above to detect the location of each vertebra and the adjacent intervertebral disc space.

Automatic detection program 112 extracts image patches corresponding to the intervertebral disc space and the vertebrae above and below the intervertebral disc space (step 606). In an embodiment, automatic detection program 112 extracts image patches corresponding to the intervertebral disc space as well as the vertebrae above and below the intervertebral disc space to capture the relative alignment of adjacent vertebrae. In an embodiment, automatic detection program 112 extracts image patches corresponding to the full vertebrae above and below the intervertebral disc space. In another embodiment, automatic detection program 112 extracts image patches corresponding to a portion of the vertebrae (e.g., the bottom half of a vertebra, the intervertebral disc space, and the top half of the next vertebra).

Automatic detection program 112 passes sequential images to the classifier (step 608). In an embodiment, automatic detection program 112 passes the image patches to a classifier, for example, classifier 422 from FIG. 4, to analyze the images. The classifier analyzes the ordered sequence of the image patches to identify changes in intervertebral spacing and vertebral alignment along the spine. In an embodiment, this is performed with an RNN classifier, e.g., an LSTM classifier. In other embodiments, this is performed with another type of classifier, for example, a combination CNN with an LSTM network, where the CNN extracts features from the series of images which are then classified by the LSTM network. The CNN can be a standard 3D CNN, or a time-distributed 2D CNN.

Automatic detection program 112 identifies changes in intervertebral spacing and vertebral alignment (step 610). In an embodiment, automatic detection program 112 detects abnormalities in the intervertebral spacing and vertebral alignment. In an embodiment, automatic detection program 112 detects abnormalities in the intervertebral spacing and vertebral alignment using a multi-output time-distributed CNN-RNN inference model that detects the presence and location of vertebral dislocations in the sequence of fully visible vertebra present in the X-ray images. The model uses an ordered sequence of vertebral pair patches (generated in step 608) as inputs. The model considers the vertebral pair images as an ordered sequence by using a time-distributed model. The model outputs a classification of a dislocation, subluxation, or not for each vertebral pair in the input sequence of vertebral images.

In an embodiment, automatic detection program 112 uses the deep learning model trained in step 508 above to detect abnormalities in the intervertebral spacing and vertebral alignment.

Automatic detection program 112 determines if other views are available (decision block 612). In an embodiment, automatic detection program 112 determines if there are any additional views to analyze. For example, if the view just analyzed is a frontal view, automatic detection program 112 determines if there is a lateral view available. In an embodiment, if automatic detection program 112 determines that there are additional views to analyze ("yes" branch, decision block 612), then automatic detection program 112 returns to step 602 to analyze the next view. In an embodiment, if automatic detection program 112 determines that there are no additional views to analyze ("no" branch, decision block 612), then automatic detection program 112 proceeds to step 614.

Automatic detection program 112 sends the results (step 614). In an embodiment, automatic detection program 112 uses the results obtained in step 610 to create a condition assessment. In an embodiment, the condition assessment is at least one of a subluxation, a dislocation, or no dislocation. In an embodiment, automatic detection program 112 creates a condition assessment individually for each view analyzed, e.g., an AP/PA view, or a lateral view. In another embodiment, automatic detection program 112 creates a condition assessment for the combined results of all views analyzed. In yet another embodiment, automatic detection program 112 creates a condition assessment for any combination of the results from the individual and combined views. In an embodiment, automatic detection program 112 sends the condition assessment to a user.

In an embodiment, automatic detection program 112 provides an alert or notification to standard medical information systems, e.g., the EMR system or PACS, when a dislocation or subluxation is detected.

In an embodiment, automatic detection program 112 ends for this cycle.

Figure 7:
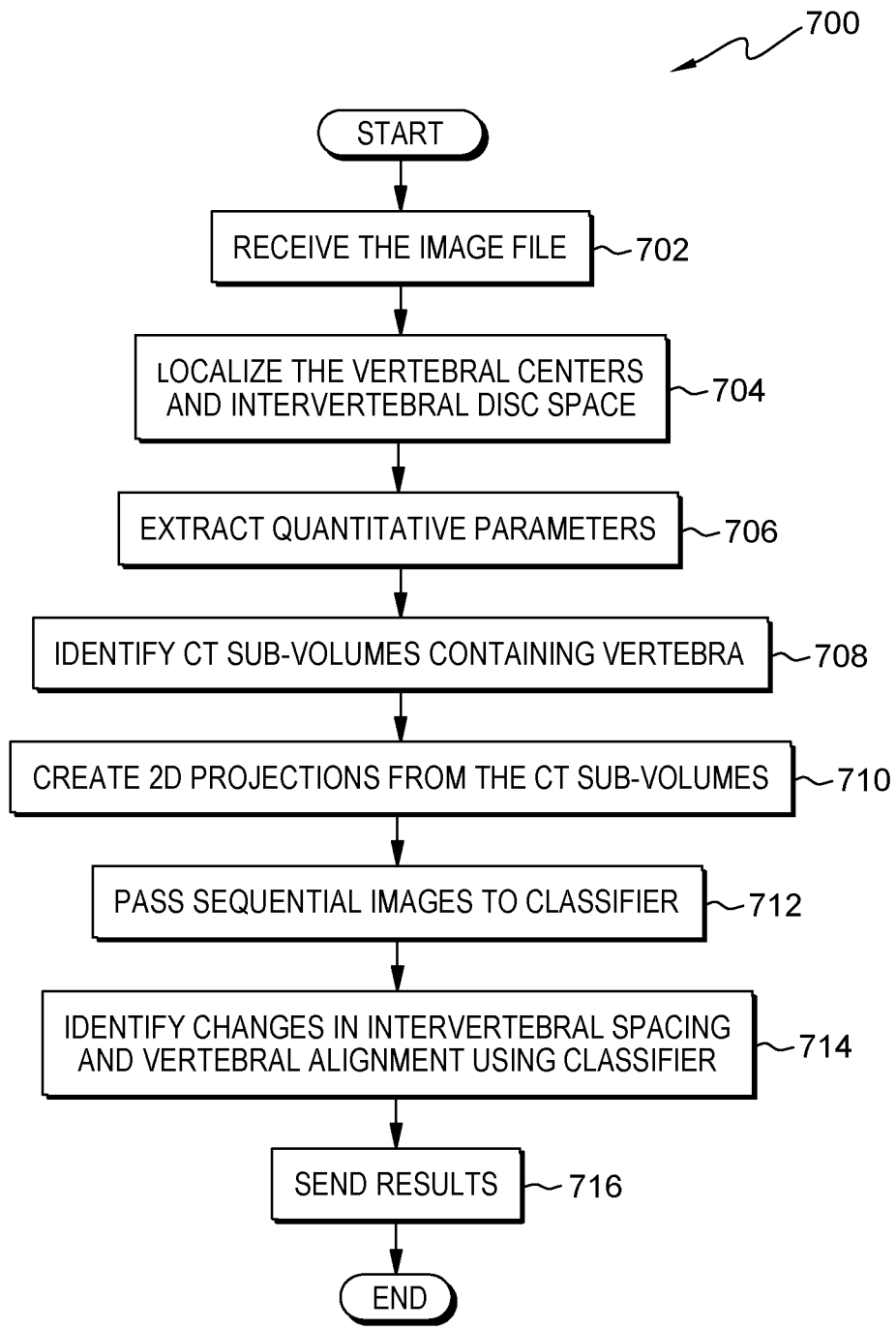
FIG. 7 is a flowchart diagram depicting operational steps for the automatic detection program for automatic detection of vertebral dislocations in 3D images, on the distributed data processing environment of FIG. 1, in accordance with an embodiment of the present invention.

FIG. 7 is a flow chart diagram of workflow 700 depicting operational steps for automatic detection program 112 for automatic detection of vertebral dislocations in 3D images. In an alternative embodiment, the steps of workflow 700 may be performed by any other program while working with automatic detection program 112. In an embodiment, automatic detection program 112 receives an image file for analysis. In an embodiment, automatic detection program 112 localizes the vertebral body centers and intervertebral disc spaces and labels each of the vertebrae (C1-L5) visible in the FOV of the CT scan. In an embodiment, automatic detection program 112 extracts quantitative parameters such as intervertebral disc sizes and volumes, and HU values in the center of vertebral bodies. In an embodiment, automatic detection program 112 identifies CT subvolumes (3D image patches) containing vertebra. In an embodiment, automatic detection program creates 2d projections from the CT subvolumes. In an embodiment, automatic detection program 112 passes the image patches to a classifier, for example, classifier 422 from FIG. 4, to analyze the images. In an embodiment, automatic detection program 112 uses ML and classification techniques to identify changes in the intervertebral spacing and vertebral alignment. In an embodiment, automatic detection program 112 sends the results.

It should be appreciated that embodiments of the present invention provide at least for automatic detection of vertebral dislocations. However, FIG. 7 provides only an illustration of one implementation and does not imply any limitations with regard to the environments in which different embodiments may be implemented. Many modifications to the depicted environment may be made by those skilled in the art without departing from the scope of the invention as recited by the claims.

It should be appreciated that the process depicted in FIG. 7 illustrates one possible iteration of the section of code performed by automatic detection program 112 for automatic detection of vertebral dislocations in 3D images, which repeats each time each time a new 3D image file is received by automatic detection program 112.

Automatic detection program 112 receives an image file (step 702). In an embodiment, automatic detection program 112 receives an image file for analysis. The format of the image file can be, for example, DICOM, NIfTI, Minc, or Analyze. In other embodiments, any appropriate image file format may be used.

Automatic detection program 112 localizes the vertebral centers and intervertebral disc space (step 704). In an embodiment, automatic detection program 112 localizes the vertebral body centers and intervertebral disc spaces and labels each of the vertebrae visible in the FOV of the CT scan.

In an embodiment, automatic detection program 112 uses the deep learning model trained in step 506 above to localize the vertebral body centers and intervertebral disc spaces.

Automatic detection program 112 extracts quantitative parameters (step 706). In an embodiment, automatic detection program 112 extracts quantitative parameters which may include, for example, the intervertebral disc sizes and volumes, and HU values in the center of vertebral bodies. In an embodiment, automatic detection program 112 uses these values in ML methods for automatic detection of dislocations.

Automatic detection program 112 identifies CT sub-volumes containing vertebra (step 708). In an embodiment, automatic detection program 112 identifies CT subvolumes containing vertebrae. Each subvolume will contain a vertebra that is to be classified in addition to at least two other adjacent vertebra to capture the relative alignment of adjacent vertebrae. For example, when determining a dislocation involving T11, the subvolume would contain T10-T11-T12 or T9-T10-T11-T12-L1, and so on. For the case of a three vertebrae subvolume, e.g. T10-T11-T12, it could include the full vertebrae above (T10) and below (T12) of vertebrae in question (T11) or a portion (e.g., the bottom half of T10, the disc space, T11, the disc space, and the top half of T12). The subvolumes are aligned either along image axes or in a local direction defined by the orientation of vertebrae in question. Subvolumes are either cuboids or cylinders.

Automatic detection program 112 creates 2D projections from the CT sub-volumes (step 710). In an embodiment, automatic detection program creates 2d projections from the CT sub-volumes. The number of generated 2D projections for each sub-volume and angles defining of those projections is in a range from 1 to 64. The projections are created using volume rendering techniques, including mean, maximum intensity projections (MIP), and sum weighted by an HU-number derived opacity function.

Automatic detection program 112 passes sequential images to the classifier (step 712). In an embodiment, automatic detection program 112 passes the 2d projection image patches created from the CT sub-volumes to a classifier, for example, classifier 422 from FIG. 4, to analyze the images. The classifier analyzes the ordered sequence of the image patches to identify changes in intervertebral spacing and vertebral alignment along the spine. In an embodiment, this is performed with an RNN classifier, e.g., an LSTM classifier. In other embodiments, this is performed with another type of classifier, for example, a combination CNN with an LSTM network, where the CNN extracts features from the series of images which are then classified by the LSTM network. The CNN can be a standard 3D CNN, or a time-distributed 2D CNN.

Automatic detection program 112 identifies changes in intervertebral spacing and vertebral alignment using the classifier (step 714). In an embodiment, automatic detection program 112 detects abnormalities in the intervertebral spacing and vertebral alignment. In an embodiment, automatic detection program 112 uses quantitative values (step 706), 3D image patches (step 708), and 2D projections (step 710) of sequential data in a classifier that considers the ordered sequence to identify changes in intervertebral spacing and vertebral alignment along the spine. In an embodiment, automatic detection program 112 detects abnormalities in the intervertebral spacing and vertebral alignment using a multi-output time-distributed CNN-RNN inference model that detects the presence and location of vertebral dislocations in the sequence of fully visible vertebra present in the X-ray images. The model uses an ordered sequence of vertebral pair patches (generated in step 710) as inputs. The model considers the vertebral pair images as an ordered sequence by using a time-distributed model. The model outputs a classification of a dislocation, subluxation, or not for each vertebral pair in the input sequence of vertebral images.

In an embodiment, automatic detection program 112 uses the deep learning model trained in step 508 above to detect abnormalities in the intervertebral spacing and vertebral alignment.

In an embodiment, automatic detection program 112 uses data obtained in steps 706, 708, and 710 to detect a dislocation on per spine section basis (cervical, thoracic, or lumbar). In this embodiment, automatic detection program 112 uses different classifiers for the different sections. In another embodiment, automatic detection program 112 uses any other different sectioning of the spine. In yet another embodiment, automatic detection program 112 uses a separate classifier for each different vertebra, in which case no sequence machine learning is used. In an embodiment, automatic detection program 112 uses classifiers that includes 3DCNN, 2DCNN, 2DCNN-RNN, 3DCNN-RNN, where RNN is RNN, LSTM, GRU or any other variation of a recurrent neural network.

In an embodiment, automatic detection program 112 uses data obtained in steps 706, 708, and 710 to create a binary classifier (i.e., dislocation present or not) and uses data from all the vertebrae to train a single classifier.

Automatic detection program 112 sends the results (step 716). In an embodiment, automatic detection program 112 uses the results obtained in step 714 to create a condition assessment. In an embodiment, the condition assessment is at least one of a subluxation, a dislocation, or no dislocation. In an embodiment, automatic detection program 112 creates a condition assessment individually for each view analyzed, e.g., an AP/PA view, or a lateral view. In another embodiment, automatic detection program 112 creates a condition assessment for the combined results of all views analyzed. In yet another embodiment, automatic detection program 112 creates a condition assessment for any combination of the results from the individual and combined views. In an embodiment, automatic detection program 112 sends the condition assessment to a user.

In an embodiment, automatic detection program 112 provides an alert or notification to standard medical information systems, e.g., the EMR system or PACS, when a dislocation or subluxation is detected.

In an embodiment, automatic detection program 112 ends for this cycle.

Figure 8:
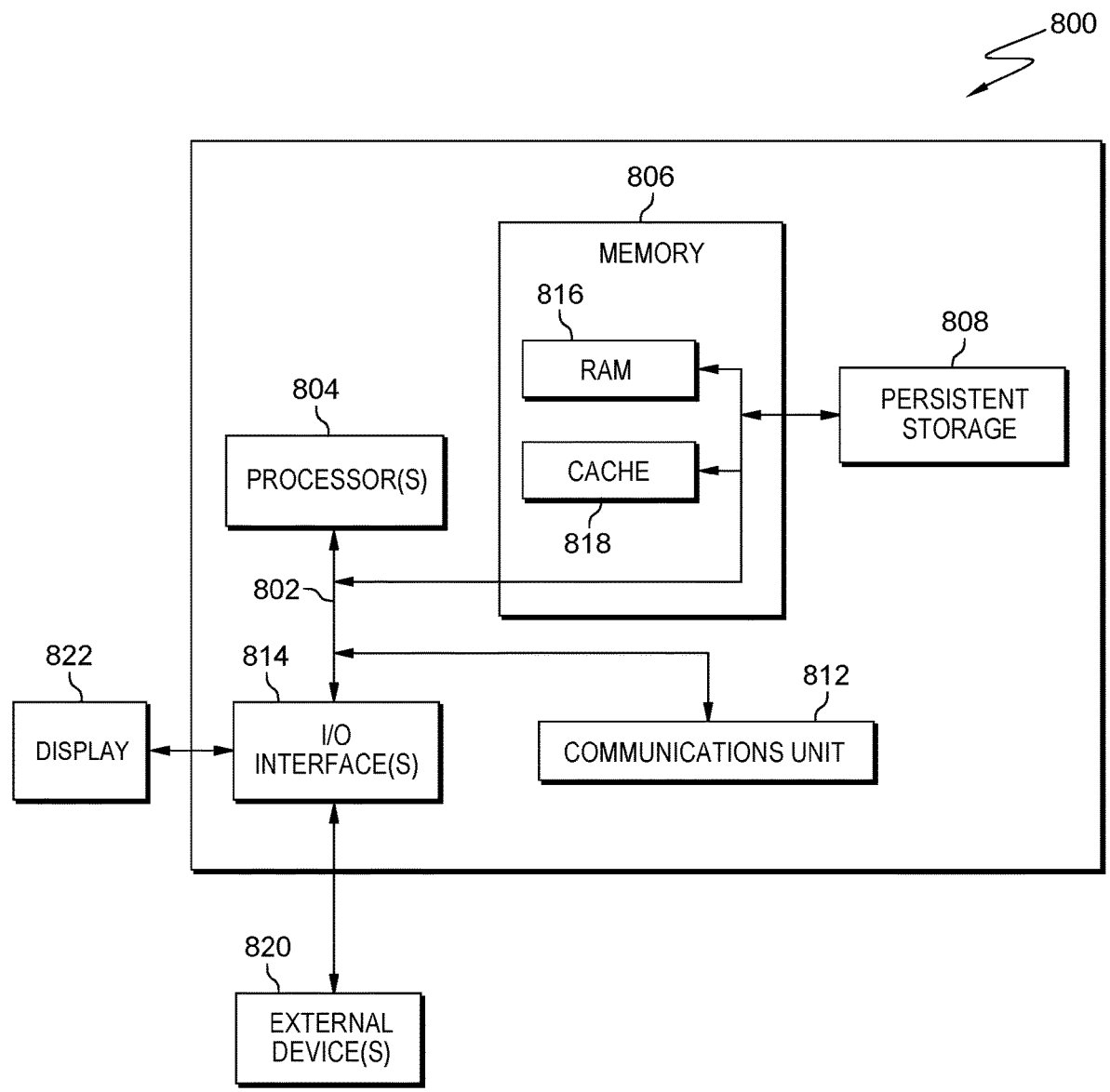
FIG. 8 depicts a block diagram of components of the computing device executing the automatic detection program within the distributed data processing environment of FIG. 1, in accordance with an embodiment of the present invention.

FIG. 8 is a block diagram depicting components of computing device 110 suitable for automatic detection program 112, in accordance with at least one embodiment of the invention. FIG. 8 displays the computer 800, one or more processor(s) 804 (including one or more computer processors), a communications fabric 802, a memory 806 including, a random-access memory (RAM) 816, and a cache 818, a persistent storage 808, a communications unit 812, I/O interfaces 814, a display 822, and external devices 820. It should be appreciated that FIG. 8 provides only an illustration of one embodiment and does not imply any limitations with regard to the environments in which different embodiments may be implemented. Many modifications to the depicted environment may be made.

As depicted, the computer 800 operates over the communications fabric 802, which provides communications between the computer processor(s) 804, memory 806, persistent storage 808, communications unit 812, and input/output (I/O) interface(s) 814. The communications fabric 802 may be implemented with an architecture suitable for passing data or control information between the processors 804 (e.g., microprocessors, communications processors, and network processors), the memory 806, the external devices 820, and any other hardware components within a system. For example, the communications fabric 802 may be implemented with one or more buses.

The memory 806 and persistent storage 808 are computer readable storage media. In the depicted embodiment, the memory 806 comprises a RAM 816 and a cache 818. In general, the memory 806 can include any suitable volatile or non-volatile computer readable storage media. Cache 818 is a fast memory that enhances the performance of processor(s) 804 by holding recently accessed data, and near recently accessed data, from RAM 816.

Program instructions for automatic detection program 112 may be stored in the persistent storage 808, or more generally, any computer readable storage media, for execution by one or more of the respective computer processors 804 via one or more memories of the memory 806. The persistent storage 808 may be a magnetic hard disk drive, a solid-state disk drive, a semiconductor storage device, read only memory (ROM), electronically erasable programmable read-only memory (EEPROM), flash memory, or any other computer readable storage media that is capable of storing program instruction or digital information.

The media used by persistent storage 808 may also be removable. For example, a removable hard drive may be used for persistent storage 808. Other examples include optical and magnetic disks, thumb drives, and smart cards that are inserted into a drive for transfer onto another computer readable storage medium that is also part of persistent storage 808.

The communications unit 812, in these examples, provides for communications with other data processing systems or devices. In these examples, the communications unit 812 includes one or more network interface cards. The communications unit 812 may provide communications through the use of either or both physical and wireless communications links. In the context of some embodiments of the present invention, the source of the various input data may be physically remote to the computer 800 such that the input data may be received, and the output similarly transmitted via the communications unit 812.

The I/O interface(s) 814 allows for input and output of data with other devices that may be connected to computer 800. For example, the I/O interface(s) 814 may provide a connection to external device(s) 820 such as a keyboard, a keypad, a touch screen, a microphone, a digital camera, and/or some other suitable input device. External device(s) 820 can also include portable computer readable storage media such as, for example, thumb drives, portable optical or magnetic disks, and memory cards. Software and data used to practice embodiments of the present invention, e.g., automatic detection program 112, can be stored on such portable computer readable storage media and can be loaded onto persistent storage 808 via the I/O interface(s) 814. I/O interface(s) 814 also connect to a display 822.

Display 822 provides a mechanism to display data to a user and may be, for example, a computer monitor. Display 822 can also function as a touchscreen, such as a display of a tablet computer.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method for automatic detection of vertebral dislocations, the computer-implemented method comprising:
   receiving, by one of more computer processors, one or more sets of training data, wherein the one or more sets of training data include an ordered sequence of radiographic image patches of vertebrae and intervertebral spaces and a location data for each vertebra and each intervertebral space in the radiographic image patches;
   training, by the one or more computer processors, one or more location deep learning models to detect a location of each vertebra of one or more vertebrae and each intervertebral space of one or more intervertebral spaces from the one or more sets of training data,
   training, by the one or more computer processors, one or more classification deep learning models to classify an ordered sequence of image patches to identify one or more vertebral anomalies of the one or more vertebrae and the one or more intervertebral spaces from the one or more sets of training data, and
   responsive to receiving one or more radiographic image files, applying, by the one or more computer processors, the one or more location deep learning models and the one or more classification deep learning models to the one or more radiographic image files to create a condition assessment.

2. The computer-implemented method of claim 1, wherein the one or more vertebral anomalies are at least one of a vertebral dislocation and a subluxation.

3. The computer-implemented method of claim 1, wherein the one or more location deep learning models and the one or more classification deep learning models include models specific to each image view.

4. The computer-implemented method of claim 1, wherein the one or more image files are one or more radiographic image files consisting of at least one of a frontal radiographic image and a lateral radiographic image.

5. The computer-implemented method of claim 1, wherein training the one or more classification deep learning models to classify the ordered sequence of image patches to identify the one or more vertebral anomalies of the one or more vertebrae and the one or more intervertebral spaces from the one or more sets of training data further comprises utilizing, by the one or more computer processors, one or more sequential characteristics and one or more morphological characteristics of the one or more spine radiographic images to identify the one or more vertebral anomalies.

6. The computer-implemented method of claim 1, wherein training the one or more classification deep learning models to classify the ordered sequence of image patches to identify the one or more vertebral anomalies of the one or more vertebrae and the one or more intervertebral spaces from the one or more sets of training data further comprises:
   training, by the one or more computer processors, the one or more classification deep learning models to identify one or more existing conditions, wherein the one or more existing conditions are selected from the group consisting of a foreign object, a spinal hardware, an external fixation device, and a spinal correction material; and
   excluding, by the one or more computer processors, the one or more existing conditions from the condition assessment.

7. The computer-implemented method of claim 1, wherein the one or more anomalies are identified based on a comparison of an analysis of the one or more image files to an analysis of a previous image file for a same patient.

8. A computer-implemented method for automatic detection of vertebral dislocations, the computer-implemented method comprising:
   receiving, by one of more computer processors, one or more sets of training data, wherein the one or more sets of training data include an ordered sequence of radiographic image patches of vertebrae and intervertebral spaces and a location data for each vertebra and each intervertebral space in the radiographic image patches;
   training, by the one or more computer processors, one or more location deep learning models to detect a location of each vertebra of one or more vertebrae and each intervertebral space of one or more intervertebral spaces from the one or more sets of training data, training, by the one or more computer processors, one or more classification deep learning models to classify an ordered sequence of image patches to identify one or more vertebral anomalies of the one or more vertebrae and the one or more intervertebral spaces from the one or more sets of training data, receiving, by the one or more computer processors, one or more computed tomography (CT) image files;

determining, by the one or more computer processors, a vertebral body center and an intervertebral disc space for each vertebra of one or more vertebrae in a field of view of the one or more CT image files;

extracting, by the one or more computer processors, one or more parameters including at least one of an intervertebral disc size, an intervertebral disc volume, and a Hounsfield unit value for each vertebra of one or more vertebrae in the field of view of the one or more CT image files;

identifying, by the one or more computer processors, one or more CT subvolumes, wherein each CT subvolume contains a vertebra;

creating, by the one or more computer processors, one or more two-dimensional projections from the one or more CT subvolumes, wherein the one or more two-dimensional projections are created using volume rendering techniques; and applying, by the one or more computer processors, the one or more location deep learning models and the one or more classification deep learning models to the one or more radiographic image files to create a condition assessment.

9. The computer-implemented method of claim 8, wherein the one or more anomalies are at least one of a vertebral dislocation and a subluxation.

10. The computer-implemented method of claim 8, wherein the one or more location deep learning models and the one or more classification deep learning models include models specific to each image view.

11. The computer-implemented method of claim 8, wherein training the one or more classification deep learning models to classify the ordered sequence of image patches to identify the one or more vertebral anomalies of the one or more vertebrae and the one or more intervertebral spaces from the one or more sets of training data further comprises utilizing, by the one or more computer processors, one or more sequential characteristics and one or more morphological characteristics of the one or more spine radiographic images to identify the one or more vertebral anomalies.

12. The computer-implemented method of claim 8, wherein training the one or more classification deep learning models to classify the ordered sequence of image patches to identify the one or more vertebral anomalies of the one or more vertebrae and the one or more intervertebral spaces from the one or more sets of training data further comprises:

training, by the one or more computer processors, the one or more classification deep learning models to identify one or more existing conditions, wherein the one or more existing conditions are selected from the group consisting of a foreign object, a spinal hardware, an external fixation device, and a spinal correction material; and excluding, by the one or more computer processors, the one or more existing conditions from the condition assessment.

13. The computer-implemented method of claim 8 further comprising providing the condition assessment to a user.

14. The computer-implemented method of claim 8, wherein the one or more anomalies are identified based on a comparison of an analysis of the one or more CT image files to an analysis of a previous CT image file for a same patient.

15. A computer system for automatic detection of vertebral dislocations, the computer system comprising:

one or more computer processors;
one or more computer readable storage media; and
program instructions stored on the one or more computer readable storage media for execution by at least one of the one or more computer processors, the stored program instructions including instructions to:

receive one or more sets of training data, wherein the one or more sets of training data include an ordered sequence of radiographic image patches of vertebrae and intervertebral spaces and a location data for each vertebra and each intervertebral space in the radiographic image patches;

train one or more location deep learning models to detect a location of each vertebra of one or more vertebrae and each intervertebral space of one or more intervertebral spaces from the one or more sets of training data, train one or more classification deep learning models to classify an ordered sequence of image patches to identify one or more vertebral anomalies of the one or more vertebrae and the one or more intervertebral spaces from the one or more sets of training data, and responsive to receiving one or more radiographic image files, apply the one or more location deep learning models and the one or more classification deep learning models to the one or more radiographic image files to create a condition assessment.

16. The computer system of claim 15, wherein the one or more vertebral anomalies are at least one of a vertebral dislocation and a subluxation.

17. The computer system of claim 15, wherein the one or more location deep learning models and the one or more classification deep learning models include models specific to each image view.

18. The computer system of claim 15, wherein the one or more image files are one or more radiographic image files consisting of at least one of a frontal radiographic image and a lateral radiographic image.

19. The computer system of claim 15, wherein training the one or more classification deep learning models to classify the ordered sequence of image patches to identify the one or more vertebral anomalies of the one or more vertebrae and the one or more intervertebral spaces from the one or more sets of training data further comprises utilizing, by the one or more computer processors, one or more sequential characteristics and one or more morphological characteristics of the one or more spine radiographic images to identify the one or more vertebral anomalies.

20. The computer system of claim 15, wherein training the one or more classification deep learning models to classify the ordered sequence of image patches to identify the one or more vertebral anomalies of the one or more vertebrae and the one or more intervertebral spaces from the one or more sets of training data further comprises:

training, by the one or more computer processors, the one or more classification deep learning models to identify one or more existing conditions, wherein the one or more existing conditions are selected from the group consisting of a foreign object, a spinal hardware, an external fixation device, and a spinal correction material; and excluding, by the one or more computer processors, the one or more existing conditions from the condition assessment.

* * * * *